United States Patent [19]

Chu et al.

[11] Patent Number: 4,985,223

[45] Date of Patent: Jan. 15, 1991

[54] CRYSTALLINE ALUMINOSILICATE

[75] Inventors: Pochen Chu, West Deptford; Joseph A. Herbst, Turnersville; Donald J. Klocke, Somerdale, all of N.J.; James Vartuli, West Chester, Pa.

[73] Assignee: Mobil Oil Corporation, Fairfax, Va.

[21] Appl. No.: 651,149

[22] Filed: Sep. 17, 1984

[51] Int. Cl.$^5$ ............................................. C01B 33/28
[52] U.S. Cl. ................................. 423/328; 423/329; 502/64; 502/77
[58] Field of Search .................... 423/326–333; 502/60, 62, 71, 77, 64

[56] References Cited

U.S. PATENT DOCUMENTS

| | | | |
|---|---|---|---|
| 4,046,859 | 9/1977 | Plank et al. | 423/329 |
| 4,086,186 | 4/1978 | Rubin et al. | 423/328 |
| 4,208,305 | 6/1980 | Kouwenhoven et al. | 423/329 |
| 4,209,499 | 6/1980 | Rubin et al. | 423/329 |
| 4,275,047 | 6/1981 | Whittam | 423/329 |
| 4,376,757 | 3/1983 | Hinnenkamp et al. | 423/326 |
| 4,420,467 | 12/1983 | Whittam | 423/329 |
| 4,495,303 | 1/1985 | Kuehl | 423/328 |

FOREIGN PATENT DOCUMENTS

| | | | |
|---|---|---|---|
| 0057049 | 8/1982 | European Pat. Off. | 423/329 |
| 0065400 | 11/1982 | European Pat. Off. | 423/328 |
| 0127399 | 12/1984 | European Pat. Off. | |
| 2024790 | 1/1980 | United Kingdom . | |
| 2079735 | 1/1982 | United Kingdom | 423/328 |

*Primary Examiner*—John Doll
*Assistant Examiner*—R. Bruce Breneman

[57] ABSTRACT

There is provided an aluminum-containing aluminosilicate zeolite corresponding to the substantially aluminum free silicate zeolite described in the Hinnenkamp et al U.S. Pat. No. 4,376,757. Also provided are methods for making this aluminosilicate zeolite and methods for the catalytic conversion of organic charges to desired products with this aluminosilicate zeolite.

13 Claims, No Drawings

CRYSTALLINE ALUMINOSILICATE

CROSS-REFERENCE TO RELATED APPLICATION

This application, is related to copending U.S. Application Ser. No. 498,224, filed May 26, 1983, abandoned, the entire disclosure of which is expressly incorporated herein by reference.

BACKGROUND

This invention relates to new crystalline aluminosilicates, to the synthesis thereof. These new crystalline aluminosilicates of the present invention would appear to be the aluminum-containing counterparts of the substantially aluminum free zeolites described in the Hinnenkamp et al U.S. Pat. No. 4,376,757, the entire disclosure of which is also expressly incorporated herein by reference. The crystalline aluminosilicates of the present invention may be synthesized in the presence of sources of alumina of limited or controlled solubility according to techniques generally described in the aforementioned U.S. Application Ser. No. 498,224.

Zeolitic materials, both natural and synthetic, have been demonstrated in the past to have catalytic properties for various types of hydrocarbon conversion. Certain zeolitic materials are ordered, porous crystalline aluminosilicates having a definite crystalline structure as determined by X-ray diffraction, within which there are a large number of smaller cavities which may be interconnected by a number of still smaller channels or pores. These cavities and pores are uniform in size within a specific zeolitic material. Since the dimensions of these pores are such as to accept for adsorption molecules of certain dimensions while rejecting those of larger dimensions, these materials have come to be known as "molecular sieves" and are utilized in a variety of ways to take advantage of these properties.

Such molecular sieves, both natural and synthetic, include a wide variety of positive ion-containing crystalline aluminosilicates. These aluminosilicates can be described as a rigid three-dimensional framework of $SiO_4$ and $AlO_4$ in which the tetrahedra are cross-linked by the sharing of oxygen atoms whereby the ratio of the total aluminum and silicon atoms to oxygen atoms is 1:2. The electrovalence of the tetrahedra containing aluminum is balanced by the inclusion in the crystal of a cation, for example an alkali metal or an alkaline earth metal cation. This can be expressed wherein the ratio of aluminum to the number of various cations, such as $Ca/2$, $Sr/2$, Na, K or Li, is equal to unity. One type of cation may be exchanged either entirely or partially with another type of cation utilizing ion exchange techniques in a conventional manner. By means of such cation exchange, it has been possible to vary the properties of a given aluminosilicate by suitable selection of the cation. The spaces between the tetrahedra are occupied by molecules of water prior to dehydration.

Prior art techniques have resulted in the formation of a great variety of synthetic zeolites. The zeolites have come to be designated by letter or other convenient symbols, as illustrated by zeolite A (U.S. Pat. No. 2,882,243), zeolite X (U.S. Pat. No. 2,882,244), zeolite Y (U.S. Pat. No. 3,130,007), zeolite ZK-5 (U. S. Pat. 3,247,195), zeolite ZK-4 (U.S. Pat. No. 3,314,752), zeolite ZSM-5 (U.S. Pat. No. 3,702,886), zeolite ZSM-11 (U.S. Pat. No. 3,709,979), zeolite ZSM-12 (U.S. Pat. No. 3,832,449), zeolite ZSM-20 (U.S. Pat. No. 3,972,983), ZSM-35 (U.S. Pat. No. 4,016,245), ZSM-38 (U.S. Pat. No. 4,046,859), and zeolite ZSM-23 (U.S. Pat. 4,076,842), merely to name a few.

The $SiO_2/Al_2O_3$ mole ratio of a given aluminosilicate zeolite is often variable. For example, zeolite X can be synthesized with $SiO_2/Al_2O_3$ ratios of from 2 to 3; zeolite Y, from 3 to about 6. In some zeolites, the upper limit of the $SiO_2/Al_2O_3$ ratio is unbounded. ZSM-5 is one such example wherein the $SiO_2/Al_2O_3$ ratio is at least 5 and up to infinity. U.S. Pat. No. 3,941,871 (Re. 29,948) discloses a porous crystalline silicate made from a reaction mixture containing no deliberately added alumina in the recipe and exhibiting the X-ray diffraction pattern characteristic of ZSM-5 type zeolites. U.S. Pat. Nos. 4,061,724, 4,073,865 and 4,104,294 describe crystalline silicates or organosilicates of varying alumina and metal content.

A number of synthetic zeolites have been prepared which may be said to be isostructural with naturally occurring zeolites. Zeolites ZSM-35 and ZSM-38 are, for instance, ferrierite-type zeolites. Zeolite ZK-20 (U.S. Pat. No. 3,459,676) is described as being isostructural with the naturally occurring zeolite levynite.

Although the term "zeolites" has sometimes been used to define materials containing silica and alumina, it is recognized that the silica and alumina portions may be replaced in whole or in part with other oxides. More particularly, $GeO_2$ is an art recognized substitute for $SiO_2$ and $B_2O_3$, $Cr_2O_3$, $Fe_2O_3$, and $Ga_2O_3$ are art recognized replacements for $Al_2O_3$. Accordingly, the term, zeolite, as used herein shall connote not only materials containing silicon and, optionally, aluminum atoms in the crystalline lattice structure thereof, but also materials which contain suitable replacement atoms for such silicon and/or aluminum. On the other hand, the term, aluminosilicate zeolite, as used herein shall define zeolite materials consisting essentially of silicon and, optionally, aluminum atoms in the crystalline lattice structure thereof, as opposed to materials which contain substantial amounts of suitable replacement atoms for such silicon and/or aluminum.

The entire disclosures of the above-mentioned U.S. patents are also expressly incorporated herein by reference.

SUMMARY

According to one aspect of the invention, there is provided a synthetic porous crystalline aluminosilicate zeolite having a silica to alumina molar ratio of from about 5 to about 500, said porous crystalline material in the uncalcined state being characterized by an x-ray diffraction pattern having values substantially as set forth in Table 1 of the specification.

According to another aspect of the invention, there is provided a method for preparing the above-mentioned synthetic porous crystalline aluminosilicate zeolite which comprises preparing a mixture capable of forming this synthetic porous crystalline material, said mixture containing sources of alkali metal ions, an oxide of aluminum, an oxide of silicon, a 2-(hydroxyalkyl)trialkylammonium cation and water and having a composition, in terms of moles, falling within the following ranges:

| | |
|---|---|
| $SiO_2/Al_2O_3$ | 20–1000 |
| $OH^-/SiO_2$ | 0.1–0.8 |
| $H_2O/OH^-$ | 20–100 |

| | |
|---|---|
| R/(R+Z) | 0.1–0.8 |
| K/(K+Na) | 0.2–1.0 | wherein R is the 2-(hydroxylkyl)trialkylammonium cation, Z is the alkali metal ion, and said $Al_2O_3$ is provided by a source of limited solubility in said reaction mixture such that said source exhibits a Degree of Solubility of less than about 20 weight percent in water solution and less than about 90 weight percent in caustic solution, and maintaining said reaction mixture under sufficient conditions until said crystalline material is formed.

According to another aspect of the invention, there is provided a process for effecting catalytic conversion of an organic charge which comprises contacting said charge under catalytic conversion conditions with a catalyst comprising a synthetic porous crystalline aluminosilicate zeolite material of the present invention.

EMBODIMENTS

The as synthesized form of the aluminosilicate zeolite of the present invention may have at least 0.5, more preferably at least 0.8, moles of 2-(hydroxyalkyl)trialkylammonium per mole of aluminum.

The term directing agent, as used herein, shall connote organic or organometallic compounds which are added to the crystallization mixture used to form a zeolite in order to influence the formation of the ultimately formed crystal lattice. At least a portion of the cations corresponding to the directing agent are bound to anionic sites of the crystal lattice in the as synthesized form of the zeolite. A directing agent which has been verified as capable of influencing the formation of the aluminosilicate zeolites of the present invention, provided that other sufficient formation conditions are met, is 2-(hydroxyalkyl)trialkylammonium chloride.

The original alkali metal cations of the as synthesized aluminosilicate zeolite can be replaced in accordance with techniques well known in the art, at least in part, by ion exchange with other cations. Preferred replacing cations include metal ions, hydrogen ions, hydrogen precursor, e.g. ammonium, ions and mixtures thereof. Particularly preferred cations are those which render the aluminosilicate zeolite catalytically active, especially for hydrocarbon conversion. Replacing cations include hydrogen, rare earth metals and metals of Groups IA, IIA, IIIA, IVA, IB, IIB, IIIB, IVB and VIII of the Periodic Table of the Elements.

A typical ion exchange technique would be to contact the synthetic aluminosilicate zeolite with a salt of the desired replacing cation or cations. Examples of such salts include the halides, e.g. chlorides, nitrates and sulfates.

Catalytically active aluminosilicate zeolite described and claimed herein, prior to calcination, has an X-ray diffraction pattern which essentially corresponds to Table I as set forth in the Hinnenkamp et al U.S. Pat. No. 4,376,757. This Table I sets forth the following observable major peaks:

TABLE 1

| Interplanar Spacing d(A) Observed | Relative Intensity |
|---|---|
| 10.90 | VS |
| 7.02 | W |
| 5.09 | W |

TABLE 1-continued

| Interplanar Spacing d(A) Observed | Relative Intensity |
|---|---|
| 4.32 | MS |
| 4.17 | W |
| 3.97 | M |
| 3.66 | M |
| 3.53 | VA |
| 3.35 | MS |
| 3.32 | MS |
| 3.23 | M |
| 2.88 | W |
| 2.78 | VW |
| 2.62 | W |
| 1.97 | W |
| 1.88 | W |
| 1.85 | W |

These values were determined by standard X-ray diffraction powder techniques. The radiation was the K-alpha doublet of copper, and a scintillation counter spectrometer with a strip chart pen recorder was used. The peak heights, I, and the positions as a function of $2\theta$, where $\theta$ is the Bragg angle, were read from the spectrometer chart. From these, the relative intensities 100 $I/I_o$, where $I_o$ is the intensity of the strongest line or peak, and d(obs.), the interplanar spacing in A corresponding to the recorded lines, were calcuated. In Table I the relative intensities are given in terms of the symbols as follows: VW=very weak (less than 10), W=weak (10–19), M=medium (20–39), MS =medium strong (40–70) and VS=very strong (greater than 70). Ion exchange of the original cations with other cations reveals substantially the same pattern with some minor shifts in interplanar spacing and variation in relative intensity. Other minor variations can occur depending on the metal to silicon ratio of the particular sample and on whether it had been subjected to thermal treatment.

A major change in the X-ray diffraction pattern has been observed when the as synthesized form of the aluminosilicate zeolite was calcined to remove the organic directing agent. Such calcination may involve heating at temperatures of about 1000° F. for about 16 hours. More particularly, for example, Table II shows X-ray diffraction data for an as synthesized form of an aluminosilicate zeolite in accordance with the present invention.

TABLE II

| LINE NUMBER | 2THETA | D(A) | I/IMAX |
|---|---|---|---|
| 1 | 8.11 | 10.91 | 100 |
| 2 | 12.58 | 7.04 | 4 |
| 3 | 13.48 | 6.57 | 2 |
| 4 | 14.07 | 6.29 | 3 |
| 5 | 14.40 | 6.15 | 1 |
| 6 | 14.80 | 5.99 | 1 |
| 7 | 16.26 | 5.45 | 1 |
| 8 | 16.98 | 5.22 | 2 |
| 9 | 17.09 | 5.19 | 2 |
| 10 | 17.46 | 5.08 | 9 |
| 11 | 17.84 | 4.97 | 2 |
| 12 | 18.21 | 4.87 | 1 |
| 13 | 20.63 | 4.31 | 19 |
| 14 | 21.24 | 4.18 | 4 |
| 15 | 22.13 | 4.02 | 1 |
| 16 | 22.44 | 3.96 | 3 |
| 17 | 22.81 | 3.90 | 2 |
| 18 | 23.92 | 3.72 | 3 |
| 19 | 24.33 | 3.66 | 9 |
| 20 | 24.51 | 3.63 | 8 |
| 21 | 25.11 | 3.55 | 17 |
| 22 | 25.34 | 3.51 | 20 |
| 23 | 26.69 | 3.34 | 7 |

TABLE II-continued

| LINE NUMBER | 2THETA | D(A) | I/IMAX |
| --- | --- | --- | --- |
| 24 | 26.95 | 3.31 | 12 |
| 25 | 27.70 | 3.22 | 7 |
| 26 | 31.03 | 2.882 | 1 |
| 27 | 32.29 | 2.772 | 1 |
| 28 | 34.22 | 2.621 | 1 |
| 29 | 35.44 | 2.533 | 1 |
| 30 | 35.96 | 2.498 | 1 |
| 31 | 38.28 | 2.351 | 1 |
| 32 | 42.08 | 2.147 | 1 |
| 33 | 44.73 | 2.026 | 1 |
| 34 | 46.04 | 1.971 | 3 |
| 35 | 48.32 | 1.884 | 1 |
| 36 | 49.13 | 1.854 | 1 |
| 37 | 51.73 | 1.767 | 1 |
| 38 | 56.25 | 1.635 | 1 |

However, after calcination of this material and conversion to the hydrogen form, this aluminosilicate zeolite showed the X-ray diffraction data as set forth in Table III.

TABLE III

| LINE NUMBER | 2THETA | D(A) | I/IMAX |
| --- | --- | --- | --- |
| 1 | 9.49 | 9.32 | 100 |
| 2 | 12.80 | 6.92 | 21 |
| 3 | 12.86 | 6.88 | 26 |
| 4 | 13.51 | 6.55 | 2 |
| 5 | 14.35 | 6.17 | 4 |
| 6 | 15.88 | 5.58 | 2 |
| 7 | 18.13 | 4.89 | 1 |
| 8 | 19.13 | 4.64 | 3 |
| 9 | 19.77 | 4.49 | 7 |
| 10 | 20.21 | 4.39 | 6 |
| 11 | 21.41 | 4.15 | 5 |
| 12 | 22.70 | 3.92 | 8 |
| 13 | 23.12 | 3.85 | 8 |
| 14 | 24.10 | 3.69 | 6 |
| 15 | 25.63 | 3.48 | 13 |
| 16 | 25.94 | 3.44 | 17 |
| 17 | 26.75 | 3.33 | 12 |
| 18 | 27.33 | 3.26 | 6 |
| 19 | 27.70 | 3.22 | 2 |
| 20 | 28.82 | 3.10 | 2 |
| 21 | 29.83 | 2.996 | 1 |
| 22 | 31.62 | 2.830 | 1 |
| 23 | 32.40 | 2.763 | 1 |
| 24 | 34.80 | 2.578 | 1 |
| 25 | 49.47 | 1.842 | 1 |

The aluminosilicate zeolites of the present invention may be considered to be aluminum-containing counterparts of the substantially aluminum free zeolites described in this Hinnenkamp et al U.S. Pat. No. 4,376,757.

The new aluminosilicate zeolite sorbs significant amounts of commonly used test adsorbate materials, i.e. cyclohexane, n-hexane and water. For example, an aluminosilicate zeolite of the present invention has been observed to sorb 1.6 weight percent cyclohexane and 1.2 weight percent n-hexane, wherein cyclohexane and n-hexane sorption are measured at 20 Torr.

The aluminosilicate zeolite of the present invention can be used either in the alkali metal form, e.g. the sodium or potassium form; the ammonium form; the hydrogen form or another univalent or multivalent cationic form. When used as a catalyst the zeolite may be subjected to thermal treatment to remove part or all of the organic constituent.

The aluminosilicate zeolite can also be used as a catalyst in intimate combination with a hydrogenating component such as tungsten, vanadium, molybdenum, rhenium, nickel, cobalt, chromium, manganese, or a noble metal such as platinum or palladium where a hydrogenation-dehydrogenation function is to be performed. Such component can be exchanged into the composition to the extent atom, aluminum, is in the structure, impregnated therein or intimately physically admixed therewith. Such component can be impregnated in or on to it such as for example, by, in the case of platinum, treating the zeolite with a solution containing a platinum metal-containing ion. Thus, suitable platinum compounds include chloroplatinic acid, platinous chloride and various compounds containing the platinum amine complex.

The aluminosilicate zeolite, especially in its metal, hydrogen and ammonium forms can be beneficially converted to another form by thermal treatment. This thermal treatment is generally performed by heating one of these forms at a temperature of at least 370° C. for at least 1 minute and generally not longer than 20 hours. While subatmospheric pressure can be employed for the thermal treatment, atmospheric pressure is desired for reasons of convenience. The thermal treatment can be performed at a temperature up to about 925° C.

The new aluminosilicate zeolite, when employed either as an adsorbent or as a catalyst in an organic compound conversion process should be dehydrated, at least partially. This can be done by heating to a temperature in the range of 200° C. to 595° C. in an inert atmosphere, such as air, nitrogen, etc. and at atmospheric, subatmospheric or superatmospheric pressures for between 30 minutes and 48 hours. Dehydration can also be performed at room temperature merely by placing the aluminosilicate zeolite in a vacuum, but a longer time is required to obtain a sufficient amount of dehydration.

The new zeolite can be prepared from a reaction mixture containing sources of alkali metal ions (Z), an oxide of aluminum, an oxide of silica, an organic or organometallic cation (R), and water. When R is a 2-(hydroxyalkyl)trialkylammonium cation wherein alkyl is composed of of one or two carbon atoms, the reaction mixture may, comprise an appropriate selection of reactants, having a composition, in terms of mole ratios, falling within the following ranges:

| Reactants | Useful | Preferred |
| --- | --- | --- |
| $SiO_2/Al_2O_3$ | 10–1000 | 20–250 |
| $OH^-/SiO_2$ | 0.1–0.8 | 0.2–0.6 |
| $H_2O/OH^-$ | 20–100 | 20–60 |
| R/(R+Z) | 0.1–0.8 | 0.2–0.6 |
| K/(K+Na) | 0.2–1.0 | 0.2–0.7 | wherein R and Z are as above defined.

The alumina sources useful herein exhibit a limited degree and rate of solubility in either water or caustic solution. This is conveniently measured as "Degree of Solubility", which is the weight percent of aluminum ions provided to the subject solution at particular conditions of temperature and time by the subject source of alumina. Degree of Solubility of said alumina source will be less than about 20 weight percent, preferably less than about 5 weight percent, in water solution determined by the following solubility test:

Five grams of alumina source (100% solid basis) are mixed and slurried with 100 grams of distilled water. The slurried mixture is heated to 100° C. and maintained at this temperature for 24 hours. The mixture is then filtered while at about 100° C. Degree of Solubility is then determined by analyzing the filtrate for aluminium ion content and drying and weighing the filtered material.

Degree of Solubility of said alumina source will be less than about 90 weight percent, preferably less than about 50 weight percent, in caustic solution determined by the following solubility test:

Five grams of alumina source (100% solid basis) are mixed and slurried with 100 grams of 5 weight percent sodium hydroxide solution (5 grams of anhydrous sodium hydroxide dissolved in 95 grams of distilled water). The slurried mixture is heated to 100° C. and maintained at this temperature for 24 hours. The mixture is then filtered while at about 100° C. Degree of solubility is then determined by analyzing the filtrate for aluminum ion content and drying and weighing the filtered material.

For either caustic or water solution, $$\text{Degree of Solubility} = \frac{\left(5 - \text{Remaining Undissolved Alumina, grams}\right)}{5} \times 100.$$

Commonly used sources of alumina for zeolite synthesis, such as, for example, sodium aluminate or aluminum sulfate, exhibit Degrees of Solubility by either of the above solubility tests of 100 weight percent. In fact, both sodium aluminate and aluminum sulfate are essentially instantaneously 100 weight percent soluble in distilled water at room temperature.

Alumina sources found to satisfy the above solubility limitations and thereby find utility in the present invention include the high temperature transition aluminas, such as, for example, kappa, theta, iota and the two delta forms of alumina; transition aluminas, such as, for example, gamma, eta and chi forms of alumina; and the tri- and monohydrated aluminas which are not predigested or reacted with alkaline earth or alkali metal hydroxide, strong mineral acids, e.g. hydrogen fluoride, etc. Such hydrated aluminas useful herein include the trihydrates known as gibbsite, bayerite and nordstrandite, and the monohydrates known as boehmite and diaspore.

Crystallization of the new aluminosilicate zeolite can be carried out at either static or stirred conditions in a suitable reactor vessel, such as for example, polypropylene jars or teflon lined or stainless steel autoclaves. A useful range of temperatures for crystallization is from about 60° C. to about 350° C. for a time of about 12 hours to about 200 days. The pH may be from about 7 to about 14.0. Thereafter, the crystals are separated from the liquid and recovered. The composition can be prepared utilizing materials which supply the appropriate oxides. Such compositions may include sodium silicate, silica hydrosol, silica gel, silicic acid, sodium hydroxide, a source of aluminum, and an appropriate organic compound. It should be realized that the reaction mixture component oxides can be supplied from more than one source. The reaction mixture can be prepared either batchwise or continuously. Crystal size and crystallization time of the new crystalline aluminosilicate zeolite will vary with the nature of the reaction mixture employed and the crystallization conditions.

In all cases, synthesis of the aluminosilicate crystals is facilitated by the presence of at least 0.01 percent, preferably 0.10 percent and still more preferably 1 percent, seed crystals (based on total weight) of crystalline product.

It will be readily understood by those of ordinary skill in the art that the above recitation of useful and preferred ranges of reactants does not constitute a warranty that all possible combinations of reactants falling within these ranges will automatically lead to the production of the aluminosilicates of the present invention. Accordingly, one must select reactants and crystallization conditions in a manner sufficient to lead to the formation of this aluminosilicate zeolite. This selection will be readily enabled by the guidance provided herein, especially with regard to the Examples recited hereinafter. In this regard, unsuccessful first attempts in the course of routine experimentation, which depart from the express reactant selections and conditions of the Examples recited hereinafter, could be followed by second attempts more closely corresponding with the express reactant selections and conditions of the Examples recited hereinafter.

It is further noted that the use of an appropriate seed crystal could theoretically change a reactant mixture not capable of forming the aluminosilicate zeolite of the present invention to a mixture capable of forming this aluminosilicate zeolite.

When a 2-(hydroxyalkyl)trialkylammonium directing agent is used, the 2-(hydroxyalkyl)trialkylammonium compound may be the hydroxide or halide, e.g. chloride, iodide or bromide. When the compound is 2-(hydroxyethyl)trimethylammonium chloride, it is called choline chloride, a preferred source of organic cations (R) in the synthesis of the aluminosilicate zeolite of the present invention.

The crystals prepared by the instant invention can be shaped into a wide variety of particle sizes. Generally speaking, the particles can be in the form of a powder, a granule, or a molded product, such as an extrudate having particle size sufficient to pass through a 2 mesh (Tyler) screen and be retained on a 400 mesh (Tyler) screen. In cases where the catalyst is molded, such as by extrusion, the crystals can be extruded before drying or partially dried and then extruded.

In the case of many catalysts, it is desired to incorporate the new aluminosilicate zeolite with another material resistant to the temperatures and other conditions employed in organic conversion processes. Such materials include active and inactive material and synthetic or naturally occurring zeolites as well as inorganic materials such as clays, silica and/or metal oxides, e.g. alumina. The latter may be either naturally occurring or in the form of gelatinous precipitates or gels including mixtures of silica and metal oxides. Use of a material in conjunction with the new aluminosilicate zeolite crystal, i.e. combined therewith, which is active, tends to improve the conversion and/or selectivity of the catalyst in certain organic conversion processes. Inactive materials suitably serve as diluents to control the amount of conversion in a given process so that products can be obtained economically and orderly without employing other means for controlling the rate of reaction. These materials may be incorporated into naturally occurring clays, e.g. bentonite and kaolin, to improve the crush strength of the catalyst under commercial operating conditions. Said materials, i.e. clays, oxides, etc., function as binders for the catalyst. It is desirable to provide a catalyst having good crush strength because in commercial use it is desirable to prevent the catalyst from breaking down into powder-like materials. These clay binders have been employed normally only for the purpose of improving the crush strength of the catalyst.

Naturally occurring clays which can be composited with the new crystal include the montmorillonite and kaolin families which include the subbentonites, and the kaolins commonly known as Dixie, McNamee, Georgia and Florida clays or others in which the main mineral constituent is halloysite, kaolinite, dickite, nacrite, or anauxite. Such clays can be used in the raw state as originally mined or initially subjected to calcination, acid treatment or chemical modification. Binders useful for compositing with the present crystal also include inorganic oxides, notably alumina.

In addition to the foregoing materials, the aluminosilicate zeolite can be composited with a porous matrix material such as silica-alumina, silica-magnesia, silica-zirconia, silica-thoria, silica-beryllia, silica-titania as well as ternary compositions such as silica-alumina-thoria, silica-alumina-zirconia, silica-alumina-magnesia and silica-magnesia-zirconia. The relative proportions of finely divided crystalline material and inorganic oxide gel matrix vary widely, with the zeolite content ranging from about 1 to about 90 percent by weight and more usually, particularly when the composite is prepared in the form of beads, in the range of about 2 to about 80 weight percent of the composite.

The aluminosilicate zeolite of the present invention is useful as catalyst component for a variety of organic, e.g. hydrocarbon, compound conversion processes. Such conversion processes include, as non-limiting examples, cracking hydrocarbons with reaction conditions including a temperature of from about 300° C. to about 700° C., a pressure of from about 0.1 atmosphere (bar) to about 30 atmospheres and a weight hourly space velocity of from about 0.1 to about 20; dehydrogenating hydrocarbon compounds with reaction conditions including a temperature of from about 300° C. to about 700° C., a pressure of from about 0.1 atmosphere to about 10 atmospheres and a weight hourly space velocity of from about 0.1 to about 20; converting paraffins to aromatics with reaction conditions including a temperature of from about 100° C. to about 700° C., a pressure of from about 0.1 atmosphere to about 60 atmospheres, a weight hourly space velocity of from about 0.5 to about 40 and a hydrogen/hydrocarbon mole ratio of from about 0 to about 20; converting olefins to aromatics, e.g. benzene, toluene and xylenes, with reaction conditions including a temperature of from about 100° C. to about 700° C., a pressure of from about 0.1 atmosphere to about 60 atmospheres, a weight hourly space velocity of from about 0.5 to about 400 and a hydrogen/hydrocarbon mole ratio of from about 0 to about 20; converting alcohols, e.g. methanol, or ethers, e.g. dimethylether, or mixtures thereof to hydrocarbons including aromatics with reaction conditions including a temperature of from about 275° C. to about 600° C., a pressure of from about 0.5 atmosphere to about 50 atmospheres and a liquid hourly space velocity of from about 0.5 to about 100; isomerizing xylene feedstock components with reaction conditions including a temperature of from about 230° C. to about 510° C., a pressure of from about 3 atmospheres to about 35 atmospheres, a weight hourly space velocity of from about 0.1 to about 200 and a hydrogen/hydrocarbon mole ratio of from about 0 to about 100; disproportionating toluene with reaction conditions including a temperature of from about 200° C. to about 760° C., a pressure of from about atmospheric to about 60 atmospheres and a weight hourly space velocity of from about 0.08 to about 20; alkylating aromatic hydrocarbons, e.g./ benzene and alkylbenzenes, in the presence of an alkylating agent, e.g., olefins, formaldehyde, alkyl halides and alcohols, with reaction conditions including a temperature of from about 340° C. to about 500° C., a pressure of from about atmospheric to about 200 atmospheres, a weight hourly space velocity of from about 2 to about 2000 and an aromatic hydrocarbon/alkylating agent mole ratio of from about 1/1 to about 20/1; and transalkylating aromatic hydrocarbons in the presence of polyalkylaromatic hydrocarbons with reaction conditions including a temperature of from about 340° C. to about 500° C., a pressure of from about atmospheric to about 200 atmospheres, a weight hourly space velocity of from about 10 to about 1000 and an aromatic hydrocarbon/polyalkylaromatic hydrocarbon mole ratio of from about 1/1 to about 16/1.

When Alpha value is examined in the Examples which follow, it is noted that the Alpha Value is an approximate indication of the catalytic cracking activity of the catalyst compared to a standard catalyst and it gives the relative rate constant (rate of normal hexane conversion per volume of catalyst per unit time). It is based on the activity of the highly active silica-alumina cracking catalyst taken as an Alpha Value of 1 (Rate Constant=0.016 sec$^{-1}$). The Alpha Test is described in U.S. Pat. No. 3,354,078 and in The Journal of Catalysis, Vol, IV, pp. 522–529 (August 1965), both incorporated herein by reference as to that description.

EXAMPLE 1

A number of individual alumina sources were tested for Degree of Solubility by the above-defined tests for both water and caustic solution. The tested sources were:

A. Primarily spray-dried and milled transition alumina with traces of alpha monodydrate alumina.
B. Spray dried alpha monohydrate alumina.
C. Dried alpha monohydrate alumina.
D. Rotary kiln dried alpha monodydrate alumina.
E. Beta trihydrate and alpha monohydrate aluminas in the form of wet filter cake.
F. Primarily transition alumina with traces of beta trihydrate and alpha monohydrate alumina.
G. Dried alpha monohydrate alumina.

Five grams of each source were individually mixed and slurried with 100 grams of distilled water, heated to 100° C. and maintained in a slurried condition at 100° C. for 24 hours. Also, five grams of each source were individually mixed and slurried with 100 grams of 5 weight percent sodium hydroxide solution (prepared by dissolving 5 grams of anhydrous sodium hydroxide in 95 grams of distilled water), heated to 100° C. and maintained in a slurried condition at 100° C. for 24 hours. The mixtures were then filtered at 100° C. and the filtrates were analyzed for aluminum ion content. The resulting filter cakes were dried and weighed. Results of this testing were as listed below:

| | Degree of Solubility, Wt. % | |
|---|---|---|
| Alumina Source | Water Solution | Caustic Solution |
| A | — | 40.4 |
| B | less than 0.2 | 31.4 |
| C | less than 0.2 | 39.8 |
| D | less than 0.2 | 28.4 |
| E | less than 0.2 | 31.2 |
| F | less than 0.2 | 45.8 |
| G | less than 0.2 | 47.2 |

-continued

| Alumina Source | Degree of Solubility, Wt. % | |
|---|---|---|
| | Water Solution | Caustic Solution |
| H | 4.2 | 49.2 |

In the following Examples 2–7, the primarily transition alumina with traces of beta trihydrate and alpha monohydrate, designated in Example 1 as alumina source F, was used as the alumina source. The following were used as silica sources:

A. An aqueous solution of colloidal silica (30 percent by weight).
B. A high surface area amorphous silica powder.

EXAMPLE 2

A solution was prepared by mixing one part (by weight) alumina, 14 parts sodium hydroxide (98% by weight), 33 parts potassium hydroxide (86% by weight) and 263 parts water. To this solution 111 parts choline chloride, 380 parts silica source A, and 28 parts ZSM-34 zeolite material were added and the mixture was stirred for approximately 15 minutes. The total mixture was then poured into teflon bottles and placed in a steam autoclave at 300° F. for seven days. The resultant crystalline material was then filtered and washed on a Buchner funnel and then dried overnight at 250° F. The analysis indicated the new aluminosilicate zeolite of the present invention having a silica to alumina molar ratio of 73.

EXAMPLE 3

A solution was prepared by mixing one part (by weight) alumina, 7 parts sodium hydroxide (98% by weight), 15 parts potassium hydroxide (86% by weight) and 128 parts water. To this solution 54 parts choline chloride and 185 parts silica source A were added and the mixture was stirred for approximately 15 minutes. The total mixture was poured into a stirred autoclave. The autoclave was heated to 320° F. with constant stirring and maintained for 72 hours. The resultant crystalline material was then filtered and washed on a Buchner funnel and then dried overnight at 250° F. The analysis indicated the new aluminosilicate zeolite of the present invention having a silica to alumina ratio of 130.

EXAMPLE 4

A solution was prepared by mixing one part (by weight) alumina, 3.5 parts sodium hydroxide (98% by weight), 8 parts potassium hydroxide (86% by weight) and 64 parts water. To this solution 27 parts choline chloride and 93 parts silica source A were added and the mixture was stirred for approximately 15 minutes. The total mixture was poured into a stirred autoclave. The autoclave was heated to 320° F. with constant stirring and maintained for 72 hours. The resultant crystalline material was then filtered and washed on a Buchner funnel and then dried overnight at 250° F. The analysis indicated the new aluminosilicate zeolite of the present invention having a silica to alumina molar ratio of 40.

EXAMPLE 5

A solution was prepared by mixing one part (by weight) alumina, 7 parts sodium hydroxide (98% by weight), 6 parts potassium hydroxide (86% by weight) and 128 parts water. This solution was added to a stirred autoclave. Another solution was prepared by mixing 54 parts choline chloride, 185 parts silica source A and 1.4 parts ZSM-34 zeolite material and then this mixture was added to the autoclave. The total mixture was stirred at room temperature for approximately 15 minutes. The autoclave was heated to 290° F. with constant stirring and maintained for 7 days. The resultant crystalline material was then filtered and washed on a Buchner funnel and then dried overnight at 250° F. The analysis indicated the new aluminosilicate zeolite of the present invention having a silica to alumina molar ratio of 78.

EXAMPLE 6

A solution was prepared by mixing one part (by weight) alumina, 7 parts sodium hydroxide (98% by weight), 15 parts potassium hydroxide (86% by weight) and 209 parts water. This solution was added to a stirred autoclave. Another solution was prepared by mixing 54 parts choline chloride and 130 parts silica source B and then was added to the autoclave. The total mixture was stirred at room temperature for approximately 15 minutes. The autoclave was heated to 320° F. with constant stirring and maintained for 72 hours. The resultant crystalline material was then filtered and washed on a Buchner funnel and then dried overnight at 250° F. The analysis indicated the new aluminosilicate zeolite of the present invention having a silica to alumina ratio of 106.

EXAMPLE 7

The zeolite from Example 5 was mixed with gamma alumina to make a mixture of 65 parts (by weight) zeolite and 35 parts alumina. Enough water was added to the mixture so that the resulting catalyst could be formed into 1/16" extrudates. These extrudates were activated by first, calcining in nitrogen at 1000° F. followed by aqueous exchanges with an ammonium nitrate solution and finally calcining in air at 1000° F. The alpha value at 528° C. was 4.

The catalyst was loaded into a straight tube (downflow) reactor (¾" I.D.) and heated to 675° F. in flowing nitrogen. A reaction mixture comprising of 50/50 (by weight) methanol/water was passed over the catalyst at a WHSV of 1 (methanol) at 0 psig. The products were analyzed and the results are as follows:

| | |
|---|---|
| Methanol Conversion | 3% |
| Selectivity (weight of hydrocarbon) | |
| Methane | 6.5 |
| $C_2=$ | 45.7 |
| $C_3=$ | 7.3 |
| $C_4=$ | 14.7 |
| $C_2$–$C_4$ Paraffins | 9.5 |

What is claimed is:

1. A synthetic porous crystalline aluminosilicate zeolite having a silica to alumina molar ratio of from about 5 to about 500, said porous crystalline material in the uncalcined state being characterized by an x-ray diffraction pattern having values substantially as set forth in Table 1 of the specification.

2. The crystalline material of claim 1 in as synthesized form.

3. The crystalline material resulting from thermal treatment of the crystalline material of claim 2.

4. A porous crystalline material comprising the crystalline material of claim 1 having original cations replaced, at least in part, with a cation or a mixture of cations selected from the group consisting of hydrogen and hydrogen precursors, rare earth metals, and metals of Groups IA, IIA, IIIA, IVA, IB, IIB, IIIB, IVB, VIB and VIII of the Periodic Table of the Elements.

5. A porous crystalline material comprising the crystalline material of claim 2 having original cations replaced, at least in part, with a cation or a mixture of cations selected from the group consisting of hydrogen and hydrogen precursors, rare earth metals, and metals of Groups IA, IIA, IIIA, IVA, IB, IIB, IIIB, IVB, VIB and VIII of the Periodic Table of the Elements.

6. The crystalline material resulting from thermal treatment of the crystalline material of claim 5.

7. A method for preparing the synthetic porous crystalline material of claim 1 which comprises preparing a mixture capable of forming a synthetic porous crystalline material of claim 1, said mixture containing sources of alkali metal ions, an oxide of aluminum, an oxide of silicon, a 2-(hydroxyalkyl)trialkylammonium cation and water and having a composition, in terms of moles, falling within the following ranges:

| | |
|---|---|
| $SiO_2/Al_2O_3$ | 20–1000 |
| $OH^-/SiO_2$ | 0.1–0.8 |
| $H_2O/OH^-$ | 20–100 |
| $R/(R+Z)$ | 0.1–0.8 |
| $K/(K+Na)$ | 0.2–1.0 | wherein R is the 2-(hydroxyalkyl)trialkylammonium cation, Z is the alkali metal ion, and said $Al_2O_3$ is provided by a source of limited solubility in said reaction mixture such that said source exhibits a Degree of Solubility of less than about 20 weight percent in water solution and less than about 90 weight percent in caustic solution, and maintaining said reaction mixture under sufficient conditions until said crystalline material is formed.

8. The method of claim 7 wherein said mixture has a composition, in terms of moles, falling within the following ranges:

| | |
|---|---|
| $SiO_2/Al_2O_3$ | 20–250 |
| $OH^-/SiO_2$ | 0.2–0.6 |
| $H_2O/OH^-$ | 20–60 |
| $R/(R+Z)$ | 0.2–0.6 |
| $K/(K+Na)$ | 0.2–0.7 |

9. The method of claim 8 wherein said mixture further comprises a sufficient amount of seed crystals.

10. The method of claim 7 wherein said sufficient conditions for maintaining said reaction mixture comprise a temperature of from about 60° C. to about 350° C. and a pH of from about 7 to about 14.0

11. The method of claim 7 wherein said source of $Al_2O_3$ is selected from the group consisting of high temperature transition alumina, transition alumina, trihydrated alumina, monohydrated alumina and mixtures thereof, said trihydrated and monohydrated alumina sources being free from prereaction with alkali or alkaline earth metal hydroxide or mineral acid.

12. The method of claim 7 wherein said source of $Al_2O_3$ exhibits a Degree of Solubility of less than about 5 weight percent in water solution and less than about 50 weight percent in caustic solution.

13. A reaction mixture capable of forming a synthetic porous crystalline material of claim 1 upon crystallization, said mixture containing sources of alkali metal ions, an oxide of aluminum and oxide of silicon, 2-(hydroxyalkyl)trialkylammonium cation and water and having a composition, in terms of moles of oxides, falling within the following ranges:

| | |
|---|---|
| $SiO_2/Al_2O_3$ | 20–250 |
| $OH^-/SiO_2$ | 0.2–0.6 |
| $H_2O/OH^-$ | 20–60 |
| $R/(R+Z)$ | 0.2–0.6 |
| $K/(K+Na)$ | 0.2–0.7 | wherein R is the 2-(hydroxyalkyl)trialkylammonium cation, Z is the alkali metal ion, and said $Al_2O_3$ is provided by a source of limited solubility in said reaction mixture such that said source exhibits a Degree of Solubility of less than about 20 weight percent in water solution and less than about 90 weight percent in caustic solution.

* * * * *